(12) United States Patent
Uetani et al.

(10) Patent No.: US 8,673,958 B2
(45) Date of Patent: Mar. 18, 2014

(54) FULLERENE DERIVATIVES

(75) Inventors: Yasunori Uetani, Tsukuba (JP); Jun Fujiwara, Ashiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/386,988

(22) PCT Filed: Jul. 20, 2010

(86) PCT No.: PCT/JP2010/062485
§ 371 (c)(1),
(2), (4) Date: Jan. 25, 2012

(87) PCT Pub. No.: WO2011/013597
PCT Pub. Date: Feb. 3, 2011

(65) Prior Publication Data
US 2012/0119198 A1   May 17, 2012

(30) Foreign Application Priority Data
Jul. 31, 2009   (JP) .................................. 2009-178996

(51) Int. Cl.
*A61K 31/403*   (2006.01)
*C07D 487/04*   (2006.01)

(52) U.S. Cl.
USPC ........................................ 514/415; 548/417

(58) Field of Classification Search
USPC ....................................................... 548/417
See application file for complete search history.

(56) References Cited

U.S. PATENT DOCUMENTS

| | | |
|---|---|---|
| 2009/0315453 A1 | 12/2009 | Kobayashi et al. |
| 2010/0045174 A1 | 2/2010 | Okabe et al. |
| 2011/0001093 A1 | 1/2011 | Itoh et al. |

FOREIGN PATENT DOCUMENTS

| | | |
|---|---|---|
| WO | WO 2008/038747 A1 | 4/2008 |
| WO | WO 2008/108430 A1 | 9/2008 |
| WO | WO 2009/035024 A1 | 3/2009 |

OTHER PUBLICATIONS

Translation of the International Preliminary Report on Patentability mailed Feb. 16, 2012 for International Application No. PCT/JP2010/063485.

Kraus, Alexander, et al., "Covalent Attachment of Various Substituents in Closest Proximity to the C60-Core: A Broad Synthetic Approach to Stable Fullerene Derivatives," Tetrahedon, 1995, pp. 9927-9940, vol. 51, No. 36.

Padinger, Franz, et al., "Effects of Postproduction Treatment on Plastic Solar Cells," Advanced Functional Materials, Jan. 2003, pp. 85-88, vol. 13, No. 1.

Sanchez, Luis, et al., "Molecular Panels for Energy Transduction in C60-Based Conjugates," Organic Letters, 2006, pp. 2451-2454, vol. 8, No. 12.

Extended European Search Report issued Dec. 5, 2012 in corresponding European Patent Application No. 10804343.1.

Nadia Camaioni, et al., "Solar cells based on poly(3-alkyl)thiophenes and [60]fullerene: a comparative study", Journal of Materials Chemistry, The Royal Society of Chemistry, Cambridge, GB, 2002, vol. 12, No. 7, pp. 2065-2070 (XP009032883).

*Primary Examiner* — Shawquia Young
(74) *Attorney, Agent, or Firm* — Sughrue Mion, PLLC

(57) ABSTRACT

A fullerene derivative having a partial structure represented by formula (1):

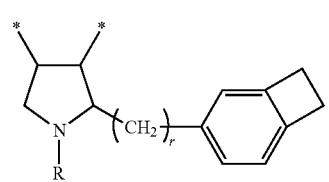

wherein R represents a monovalent group, and r represents an integer of 0 to 4, in particular, a fullerene derivative, which has one to four structures represented by formula (1), can be applied to an organic photoelectric conversion element having a high open-circuit voltage and is therefore suitable for an organic thin-film solar cell or an organic photosensor, and thus it is extremely useful.

9 Claims, No Drawings

FULLERENE DERIVATIVES

TECHNICAL FIELD

The present invention relates to a fullerene derivative, and an organic photoelectric conversion element using the same.

BACKGROUND ART

Application of organic semiconductor materials having charge (electron, hole) transporting properties to organic photoelectric conversion elements (organic solar cells, photosensors, and the like) has been examined and, for example, an organic solar cell using fullerene derivatives has been examined. For example, a [6,6]-phenyl C61-butyric acid methyl ester (hereinafter sometimes referred to as [60]-PCBM) is known as a fullerene derivative (see Advanced Functional Materials, Vol. 13 (2003), p. 85).

SUMMARY OF THE INVENTION

However, an organic photoelectric conversion element containing [60]-PCBM has a problem that it does not necessarily have a sufficient Voc (open-circuit voltage).

The present invention provides an organic photoelectric conversion element having a high Voc (open-circuit voltage).

That is, the present invention provides a fullerene derivative having a partial structure represented by formula (1):

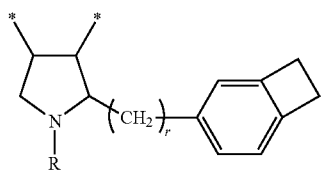

wherein R represents a monovalent group, and r represents an integer of 0 to 4.

Mode for Carrying Out the Invention

The present invention will be described in detail below. The fullerene derivative of the present invention has a partial structure represented by formula (1). R in formula (1) represents a monovalent group, and specific examples thereof include an alkyl group, an alkoxy group, an aryl group, a halogen atom, a heterocyclic group, a group represented by formula (3) or a group having an ester structure.

The alkyl group represented by R usually has 1 to 20 carbon atoms, and may be linear or branched, or cyclic (cycloalkyl). Specific examples of the alkyl group include a methyl group, an ethyl group, a propyl group, an isopropyl group, a butyl group, an isobutyl group, a tert-butyl group, a sec-butyl group, a 3-methylbutyl group, a pentyl group, a hexyl group, a 2-ethylhexyl group, a heptyl group, an octyl group, a nonyl group, a decyl group and a lauryl group. Regarding the monovalent group, a hydrogen atom(s) in the alkyl group may be substituted with a halogen atom(s), and specific examples thereof include a monohalomethyl group, a dihalomethyl group, a trihalomethyl group and a pentahaloethyl group. Among the halogen atoms, a fluorine atom is preferable. Specific examples of the alkyl group whose hydrogen atom(s) is substituted with a fluorine atom(s) include a trifluoromethyl group, a pentafluoroethyl group, a perfluorobutyl group, a perfluorohexyl group and a perfluorooctyl group.

The alkoxy group represented by R usually has 1 to 20 carbon atoms, and may be a linear or branched group or a cycloalkyloxy group. Specific examples of the alkoxy group include a methoxy group, an ethoxy group, a propoxy group, an isopropoxy group, a butoxy group, an isobutoxy group, a sec-butoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group and a lauryloxy group. Regarding the monovalent group, a hydrogen atom(s) in the alkoxy group may be substituted with a halogen atom(s). Among the halogen atoms, a fluorine atom is preferable. Specific examples of the alkoxy group whose hydrogen atom(s) is substituted with a fluorine atom(s) include a trifluoromethoxy group, a pentafluoroethoxy group, a perfluorobutoxy group, a perfluorohexyloxy group and a perfluorooctyloxy group.

The aryl group represented by R is a hydrocarbon group which is an aromatic ring, and usually has 6 to 60 carbon atoms. The aryl group may have a substituent(s), and examples of the substituent include a linear or branched alkyl group having 1 to 20 carbon atoms or a cyclic alkyl group (cycloalkyl group) having 3 to 20 carbon atoms, an alkoxy group containing a linear, branched or cyclic alkyl group having 1 to 20 carbon atoms in the structure, and a halogen atom. Specific examples of the aryl group include a phenyl group, a $C_1$-$C_{12}$ alkoxyphenyl group ($C_1$-$C_{12}$ means that the number of carbon atoms is from 1 to 12, the same shall apply hereinafter), a $C_1$-$C_{12}$ alkylphenyl group, a 1-naphthyl group and a 2-naphthyl group, and an aryl group having 6 to 20 carbon atoms is preferable, and a $C_1$-$C_{12}$ alkoxyphenyl group and a $C_1$-$C_{12}$ alkylphenyl group are more preferable. Among the halogen atoms, a fluorine atom is preferable.

Examples of the halogen atom represented by R include the respective atoms of fluorine, chlorine, bromine and iodine.

Examples of the heterocyclic group represented by R include a thienyl group, a pyridyl group, a furyl group, a piperidyl group, a quinolyl group, an isoquinolyl group and a pyrrolyl group. A monovalent aromatic heterocyclic group is preferable.

Examples of the group having an ester structure represented by R include a group obtained by removing one hydrogen atom from methyl butyrate, a group obtained by removing one hydrogen atom from butyl butyrate, a group obtained by removing one hydrogen atom from isopropyl butyrate, and a group obtained by removing one hydrogen atom from 3-ethylthienyl butyrate.

An aspect of the group having an ester structure is a group represented by formula (4):

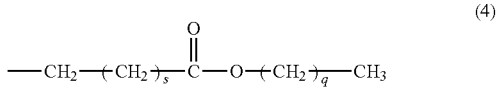

wherein s represents an integer of 0 to 10, and q represents an integer of 0 to 10.

The monovalent group represented by R may be a group represented by formula (3). From the viewpoint of solubility of a fullerene derivative, R is preferably a group represented by formula (3):

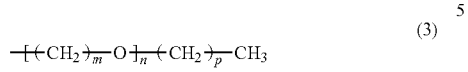
(3)

wherein m represents an integer of 1 to 6, n represents an integer of 1 to 4, and p represents an integer of 0 to 5. When a plurality of structures represented by —(CH$_2$—)$_m$—O— are present, m in the structures may be the same numerical value, or mutually different numerical values.

In formula (3), m is preferably 2 from the viewpoint of availability of a raw material. From the viewpoint of charge transporting properties, p is preferably an integer of 0 to 3.

The fullerene derivative of the present invention preferably has one to four structures represented by formula (1). From the viewpoint of ease of synthesis, the fullerene derivative more preferably has one or two structures represented by formula (1).

In the fullerene derivative of the present invention, specific examples of the derivative of C60 fullerene include the following compounds.

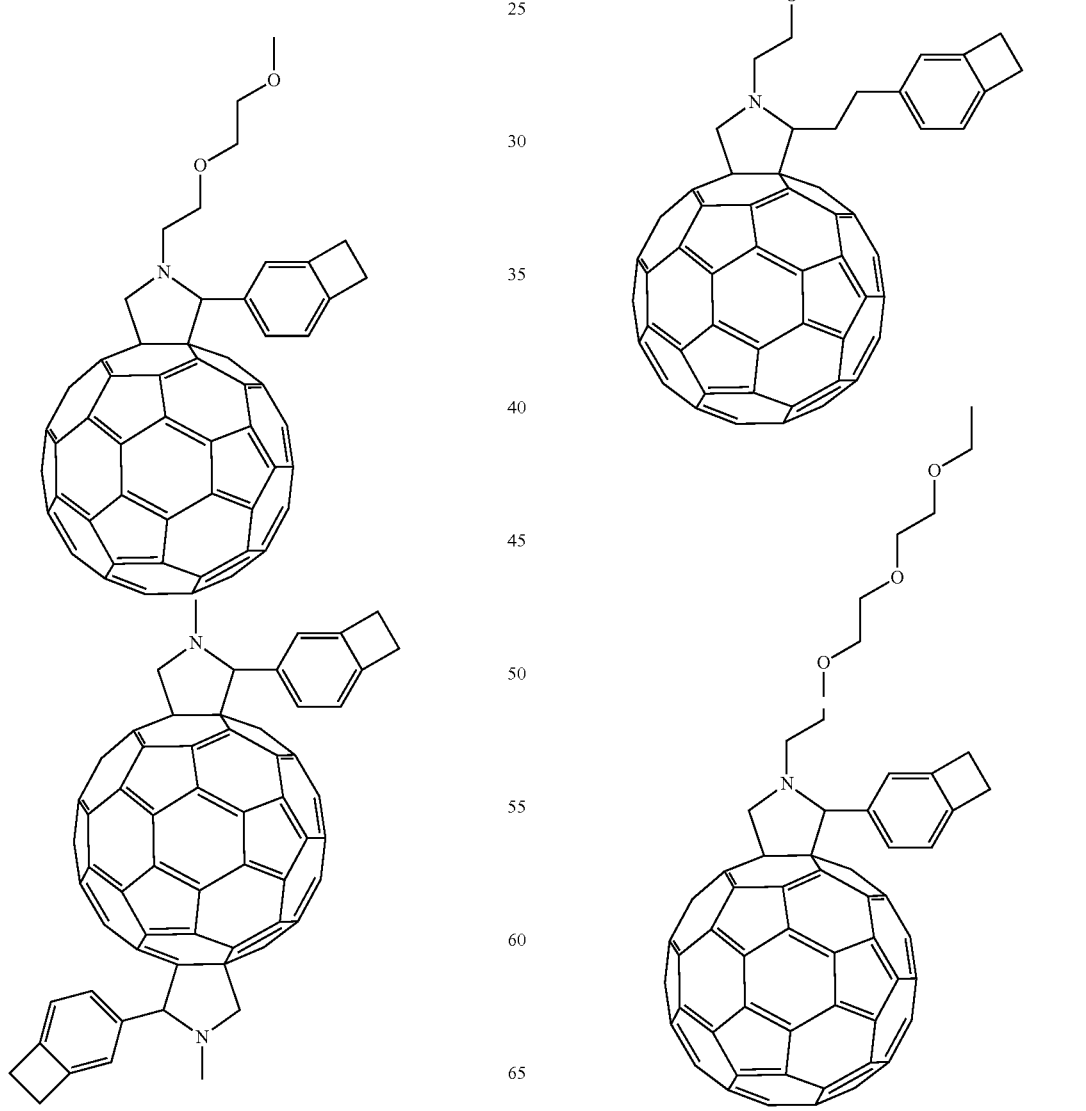

-continued

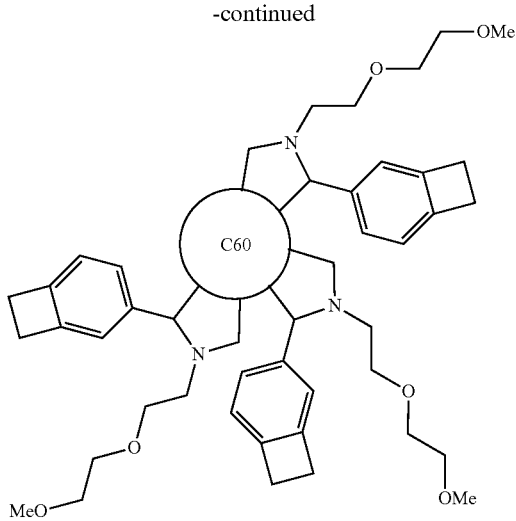

In the above compounds, the C60 ring represents a fullerene ring having 60 carbon atoms.

In the fullerene derivative of the present invention, specific examples of the derivative of C70 fullerene include the following compound.

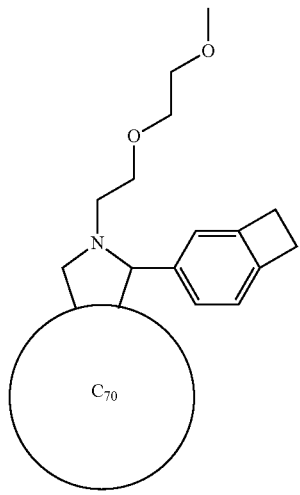 [SMILES: CCN(CCOCCOC)C(C)c1ccc2c(c1)CC2 ; "C70"]

In the above compound, the C70 ring represents a fullerene ring having 70 carbon atoms.

The fullerene derivative of the present invention is preferably a fullerene derivative represented by formula (2a) or (2b):

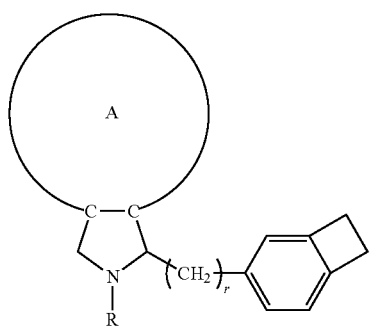

(2a)

wherein ring A represents a fullerene skeleton having 60 or more carbon atoms, and R and r have the same meanings as defined above, and

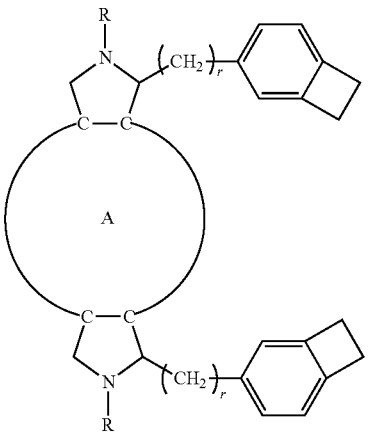

(2b)

wherein ring A represents a fullerene skeleton having 60 or more carbon atoms, R and r have the same meanings as defined above, a plurality of R's may be the same or different, and a plurality of r's may be the same or different.

In formulas (2a) and (2b), ring A is preferably $C_{60}$ fullerene or $C_{70}$ fullerene from the viewpoint of availability of a raw material.

An organic photoelectric conversion element produced using the fullerene derivative of the present invention exhibits increased photoelectric conversion efficiency.

The fullerene derivative of the present invention can be synthesized, for example, by a 1,3-dipolar cycloaddition reaction of an iminium cation, which is generated from imine formed from a glycine derivative and an aldehyde through decarboxylation, with fullerene (Prato reaction, Accounts of Chemical Research, Vol. 31, 1998, pp. 519-526).

Examples of the glycine derivative used herein include N-methoxymethylglycine and N-(2-(2-methoxyethoxy)ethyl)glycine. The used amount of the glycine derivative is usually within a range from 0.1 to 10 mol, and preferably within a range from 0.5 to 3 mol, based on 1 mol of fullerene. Examples of the aldehyde, which is the other raw material, include an aldehyde represented by formula (5):

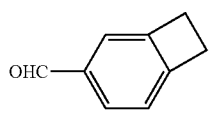

(5)

The used amount of the aldehyde is usually within a range from 0.1 to 10 mol, and preferably within a range from 0.5 to 4 mol, based on 1 mol of fullerene.

A reaction for synthesizing the fullerene derivative by the present invention is usually carried out in a solvent. Examples of usable solvents include those inert to the synthesis reaction, such as toluene, xylene, hexane, octane and chlorobenzene. The used amount of the solvent is usually within a range from 1- to 100,000-fold amount by weight, relative to fullerene.

In the reaction, for example, the glycine derivative, the aldehyde and fullerene may be mixed in a solvent and then subjected to a heating reaction, and the reaction temperature is usually within a range from 50 to 350° C. The reaction time is usually from 30 minutes to 50 hours.

After the heating reaction, the reaction mixture is left standing to cool to room temperature and the solvent is distilled off under reduced pressure using a rotary evaporator, and then the obtained solid matter is separated and purified by silica gel flash column chromatography, and thus the objective fullerene derivative can be obtained.

Since the compound having a benzocyclobutene structure contained in formula (1) has thermal cross-linkability, the fullerene derivative of the present invention can be cross-linked by heating. From the viewpoint of increasing thermostability of the organic photoelectric conversion element, the fullerene derivative of the present invention is preferably cross-linked by heating.

Since the fullerene derivative can be used in the organic photoelectric conversion element together with an electron-donating compound, the present invention also provides a composition containing the fullerene derivative and the electron-donating compound.

Since the composition is used by application, the electron-donating compound is preferably a polymer compound, for example, polyvinyl carbazole and a derivative thereof, polysilane and a derivative thereof, a polysiloxane derivative having an aromatic amine in a side chain or a main chain, polyaniline and a derivative thereof, polythiophene and a derivative thereof, polypyrrole and a derivative thereof, polyphenylene vinylene and a derivative thereof, polythienylene vinylene and a derivative thereof, or polyfluorene and a derivative thereof.

From the viewpoint of conversion efficiency, the electron-donating compound is preferably a polymer compound having a repeating unit selected from the group consisting of repeating units represented by formulas (10) and (11), and more preferably a polymer compound having a repeating unit represented by formula (10):

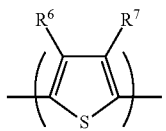

(10)

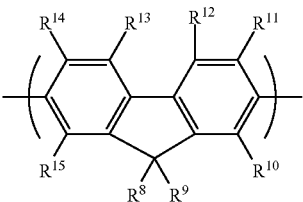

(11)

wherein $R^6$, $R^7$, $R^8$, $R^9$, $R^{10}$, $R^{11}$, $R^{12}$, $R^{13}$, $R^{14}$ and $R^{15}$ are the same or different and represent a hydrogen atom, an alkyl group, an alkoxy group or an aryl group.

In the case where $R^6$ and $R^7$ in formula (10) are alkyl groups, specific examples thereof include the same alkyl groups as those described above as for R. In the case where $R^6$ and $R^7$ are alkoxy groups, specific examples thereof include the same alkoxy groups as those described above as for R. In the case where $R^6$ and $R^7$ are aryl groups, specific examples thereof include the same aryl groups as those described above as for R.

In formula (10), at least one of $R^6$ and $R^7$ is preferably an alkyl group having 1 to 20 carbon atoms, and more preferably an alkyl group having 4 to 8 carbon atoms, from the viewpoint of conversion efficiency.

In the case where $R^8$ to $R^{15}$ in formula (11) are alkyl groups, specific examples thereof include the same alkyl groups as those described above as for R. In the case where $R^8$ to $R^{15}$ are alkyl groups, specific examples thereof include the same alkoxy groups as those described above as for R. In the case where $R^8$ to $R^{15}$ are aryl groups, specific examples thereof include the same aryl groups as those described above as for R.

In formula (11), $R^{10}$ to $R^{15}$ are preferably a hydrogen atom, from the viewpoint of ease of synthesis of the monomer. From the viewpoint of conversion efficiency, $R^8$ and $R^9$ are preferably an alkyl group having 1 to 20 carbon atoms or an aryl group having 6 to 20 carbon atoms, and more preferably an alkyl group having 5 to 8 carbon atoms or an aryl group having 6 to 15 carbon atoms.

The amount of the fullerene derivative contained in the composition of the present invention is preferably from 10 to 1,000 parts by weight, and more preferably from 50 to 500 parts by weight based on 100 parts by weight of the electron-donating compound.

The present invention also provides an organic photoelectric conversion element, and the organic photoelectric conversion element includes a pair of electrodes, at least one of which is transparent or translucent, and a layer containing a fullerene derivative used in the present invention between the electrodes. The fullerene derivative used in the present invention can also be used as an electron-accepting compound and an electron-donating compound, and is preferably used as the electron-accepting compound.

An operation mechanism of the organic photoelectric conversion element will be described below. Energy of incident light from a transparent or translucent electrode is absorbed in the electron-accepting compound and/or the electron-donating compound to form an exciton in which an electron and a hole are bonded. When the thus formed exciton moves and reaches a heterojunction interface where the electron-accepting compound and the electron-donating compound are adjacent to each other, the electron and the hole are separated from each other due to a difference in HOMO energy and LUMO energy of the respective compounds at the interface, and thus a charge (electron and hole) capable of independently moving is generated. The thus generated charge can be extracted outside as electric energy (current) by moving to the electrode, respectively.

Specific example of the organic photoelectric conversion element of the present invention is preferably any one of:

1. an organic photoelectric conversion element comprising a pair of electrodes, at least one of which is transparent or translucent, a first layer containing the fullerene derivative of the present invention as an electron-accepting compound provided between the electrodes, and a second layer containing an electron-donating compound provided adjacent to the first layer;

2. an organic photoelectric conversion element comprising a pair of electrodes, at least one of which is transparent or translucent, and at least one layer containing the fullerene derivative of the present invention as an electron-accepting compound, and an electron-donating compound provided between the electrodes;

3. an organic photoelectric conversion element comprising a pair of electrodes, at least one of which is transparent or translucent, a first layer formed by cross-linking the fullerene derivative of the present invention through heating provided between the electrodes, and a second layer containing an electron-donating compound provided adjacent to the first layer; and 4. an organic photoelectric conversion element comprising a pair of electrodes, at least one of which is transparent or translucent, and at least one layer formed by cross-linking the composition of the present invention, which contains a fullerene derivative and an electron-donating compound, through heating provided between the electrodes.

The second organic photoelectric conversion element is preferable since it contains many heterojunction interfaces. The organic photoelectric conversion element of the present invention may be provided with an additional layer between at least one of the electrodes and a layer containing a fullerene derivative used in the present invention. Examples of the additional layer include a charge transporting layer which transports a hole or an electron.

In the second organic photoelectric conversion element, the proportion of the fullerene derivative in the organic layer containing a fullerene derivative and an electron-donating compound is preferably from 10 to 1,000 parts by weight, and more preferably from 50 to 500 parts by weight, based on 100 parts by weight of the electron-donating compound.

In the second organic photoelectric conversion element, the organic layer containing a fullerene derivative and an electron-donating compound can be produced by using a composition containing a fullerene derivative and an electron-donating compound.

The layer containing a fullerene derivative, which can be used in the organic photoelectric conversion element of the present invention, is preferably formed of an organic thin film containing the fullerene derivative. The thickness of the organic thin film is usually from 1 nm to 100 μm, preferably from 2 nm to 1,000 nm, more preferably from 5 nm to 500 nm, and still more preferably from 20 nm to 200 nm.

One method for producing a layer formed by cross-linking a fullerene derivative used in the organic photoelectric conversion elements of the above 3. and 4. is a method in which a solution containing a fullerene derivative of the present invention and a solvent is applied on one of electrodes (anode or cathode) to form an organic layer, and then the organic layer is heated. Another method is a method in which a solution containing a composition of the present invention and a solvent is applied on one of electrodes to form an organic layer, and then the organic layer is heated. In an aspect of these organic photoelectric conversion elements, the layer formed by cross-linking the fullerene derivative functions as an active layer.

The layer formed by cross-linking the fullerene derivative may be formed from an organic thin film containing a cross-linked fullerene derivative. The thickness of the organic thin film is usually from 1 nm to 100 preferably from 2 nm to 1,000 nm, more preferably from 5 nm to 500 nm, and still more preferably from 20 nm to 200 nm.

The organic photoelectric conversion element of the present invention is usually formed on a substrate. The material of this substrate may be a material which forms an electrode and does not cause a chemical change in case of forming a layer of an organic substance. Examples of the material of the substrate include glass, plastic, a polymer film and silicone. In case of an opaque substrate, an opposite electrode (i.e., an electrode which is more far from the substrate) is transparent or semitransparent.

Examples of the material of the transparent or translucent electrode include a conductive metal oxide film and a translucent metal thin film. Specifically, a film (NESA, for example) produced using a conductive material composed of indium oxide, zinc oxide, tin oxide, or indium tin oxide (ITO) or indium zinc oxide which is a composite thereof, gold, platinum, silver or copper is used. Among these materials, ITO, indium zinc oxide and tin oxide are preferable. Examples of the method for producing an electrode include a vacuum deposition method, a sputtering method, an ion plating method, and a plating method.

An organic transparent conductive film of polyaniline and a derivative thereof, polythiophene and a derivative thereof or the like may be used as an electrode material.

The electrode material of one electrode of a pair of electrodes is preferably a material having a small work function. The electrode containing the material having a small work function may be transparent or translucent. Examples of the material to be used include metals such as lithium, sodium, potassium, rubidium, cesium, magnesium, calcium, strontium, barium, aluminum, scandium, vanadium, zinc, yttrium, indium, cerium, samarium, europium, terbium and ytterbium, alloys of two or more metals among them, alloys of one or more metals among them and one or more metals among gold, silver, platinum, copper, manganese, titanium, cobalt, nickel, tungsten and tin, graphite and a graphite intercalation compound. Examples of the alloy include a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The additional layer, which may be provided between an electrode and a layer containing a fullerene derivative used in the present invention, may be a buffer layer. Examples of the material used as the buffer layer include alkali metals such as lithium fluoride, halides of alkali earth metals, and oxides such as titanium oxide. In case of using an inorganic semiconductor, it is also possible to use in the form of fine particles.

There is no particular limitation on the method for producing an organic thin film, and examples of the method include a method by formation of a film from a solution containing a fullerene derivative used in the present invention.

There is no particular limitation on the solvent used in formation of a film from a solution, as long as the solvent dissolves a fullerene derivative used in the present invention. Examples of the solvent include hydrocarbon solvents such as toluene, xylene, mesitylene, tetralin, decalin, bicyclohexyl, butylbenzene, sec-butylbenzene and tert-butylbenzene; halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane; halogenated unsaturated hydrocarbon solvents such as chlorobenzene, dichlorobenzene and trichlorobenzene; and ether solvents such as tetrahydrofuran and tetrahydropyran. The fullerene derivative can be usually dissolved in the solvent in the concentration of 0.1% by weight or more.

The solution may further contain a polymer compound. Specific examples of the solvents used in the solution include the solvents described above. From the viewpoint of solubility of the polymer compound, aromatic hydrocarbon solvents are preferable, and toluene, xylene and mesitylene are more preferable.

It is possible to use coating methods such as a spin coating method, a casting method, a microgravure coating method, a gravure coating method, a bar coating method, a roll coating method, a wire bar coating method, a dip coating method, a spray coating method, a screen printing method, a flexo printing method, an offset printing method, an inkjet printing method, a dispenser printing method, a nozzle coating method and a capillary coating method, for forming a film from a solution. Among these methods, a spin coating method, a flexo printing method, an inkjet printing method and a dispenser printing method are preferable.

The organic photoelectric conversion element is irradiated with light such as sunlight from a transparent or semitransparent electrode to generate a photoelectromotive force between electrodes, and thus making it possible to operate as an organic thin-film solar cell. It is also possible to use the organic thin-film solar cell as an organic thin-film solar cell module by integrating a plurality of organic thin-film solar cells.

When light is radiated from a transparent or semitransparent electrode in a state where a voltage is applied between electrodes, a photocurrent flows, and thus making it possible to operate the organic photoelectric conversion element as an organic photosensor. It is also possible to use the organic photosensor as an organic image sensor by integrating a plurality of organic photosensors.

EXAMPLES

The present invention will be described in more detail below by way of examples, but the present invention is not limited thereto.

Regarding reagents and solvents used in the synthesis, commercially available products were used as it is, or products purified by distillation in the presence of a desiccant were used. $C_{60}$ fullerene manufactured by Frontier Carbon Corporation was used. NMR spectra were measured using MH500 manufactured by JEOL, Ltd. and tetramethylsilane (TMS) was used as an internal standard. Infrared absorption spectra were measured using FT-IR 8000 manufactured by Shimadzu Corporation. MALDI-TOF MS spectra were measured using AutoFLEX-T2 manufactured by BRUKER Corporation.

Example 1

Synthesis of Fullerene Derivative A (Synthesis of Benzyl[2-(2-hydroxyethoxy)ethylamino] Acetate)

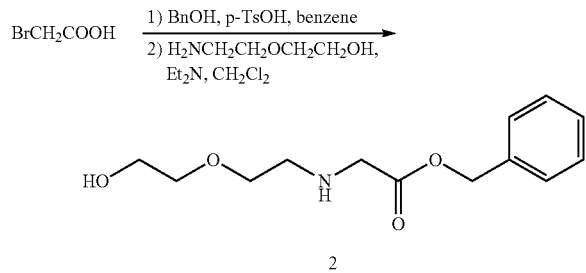

[First Step]:
In a two-necked flask equipped with a Dean-Stark trap, bromoacetic acid (20.8 g, 150 mmol), benzyl alcohol (16.2 g, 150 mmol), paratoluenesulfonic acid (258 mg, 1.5 mmol) and benzene (300 mL) were charged, followed by dehydration condensation at 120° C. for 24 hours. The solvent was distilled off under reduced pressure using an evaporator, and then purified by silica gel flash column chromatography (hexane/ethyl acetate=10/1, 5/1) to quantitatively obtain bromoacetic acid benzyl ester (34.3 g, 150 mmol) as a yellow oily product.

$R_f$ 0.71 (hexane/ethyl acetate=4/1);
$^1$H MR (500 MHz, ppm, $CDCl_3$) δ3.81 (s, 2H), 5.14 (s, 2H), 7.31 (s, 5H); $^{13}$C NMR (125 MHz, ppm, $CDCl_3$) δ25.74, 67.79, 128.27, 128.48, 128.54, 134.88, 166.91;
IR (neat, $cm^{-1}$) 2959, 1751, 1458, 1412, 1377, 1167, 972, 750, 698.

[Second Step]:
Under an argon atmosphere, triethylamine (17 mL, 120 mmol) was added to a dichloromethane (90 mL) solution of bromoacetic acid benzyl ester (13.7 g, 60 mmol) at 0° C. and the obtained mixed liquid was stirred at the same temperature for 20 minutes. Then, a dichloromethane (40 mL) solution of 2-(2-aminoethoxy)ethanol (12 mL, 120 mmol) was added, followed by stirring at room temperature for 4 hours. Then, the organic layer was washed three times with water and dried over anhydrous magnesium sulfate. After the solvent was distilled off under reduced pressure using an evaporator, the residue was purified by silica gel flash column chromatography (eluent: ethyl acetate/methanol=1/0, 10/1, 5/1) to obtain benzyl[2-(2-hydroxyethoxy)ethylamino] acetate (12.2 g, 48.0 mmol) as a colorless oily product with a yield of 80%.

$R_f$ 0.48 (ethyl acetate/methanol=2/1);
$^1$H NMR (500 MHz, ppm, $CDCl_3$) δ2.83 (t, 2H, J=5.1 Hz), 3.50 (s, 2H), 3.52 (t, 2H, J=4.6 Hz), 3.58 (t, 2H, J=5.0 Hz), 3.65 (t, 2H, J=4.6 Hz), 5.11 (s, 2H), 7.28-7.30 (m, 5H); $^{13}$C NMR (125 MHz, ppm, $CDCl_3$) δ48.46, 50.25, 61.29, 66.38, 69.80, 72.23, 126.63, 128.12, 128.37, 135.30, 171.78;
IR (neat, $cm^{-1}$) 3412, 2880, 1719, 1638, 1560, 1508, 1458, 1067, 669.

(Synthesis of [2-(2-methoxyethoxy)ethylamino]acetic Acid (1))

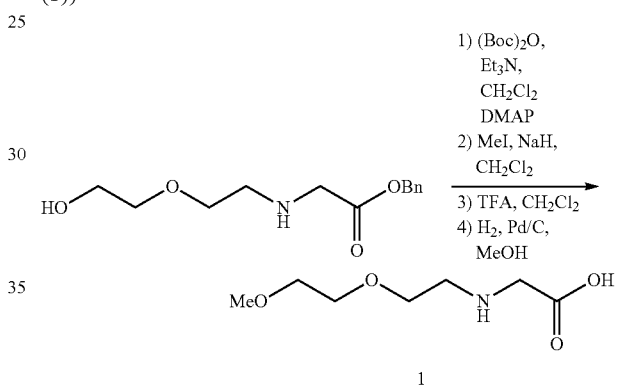

[First Step]:
Under an argon atmosphere, triethylamine (4.3 mL, 31 mmol) was added to a dichloromethane (50 mL) solution of benzyl[2-(2-hydroxyethoxy)ethylamino] acetate (6.58 g, 26 mmol) at 0° C., and then 4-(N,N-dimethylamino)pyridine (32 mg, 0.26 mmol) was added. After stirring the obtained mixed liquid for 20 minutes, a dichloromethane (10 mL) solution of di-tert-butyl dicarbonate (6.77 g, 31 mmol) was added dropwise thereto. The reaction mixed liquid was stirred at room temperature for 4 hours and poured into an Erlenmeyer flask charged with water, thereby terminating the reaction, and then the reaction liquid was extracted three times with diethylether. The organic layer was dried, concentrated under reduced pressure and then purified by silica gel flash column chromatography (eluent: hexane/ethyl acetate=3/1, 2.5/1, 2/1) to obtain benzyl{tert-butoxycarbonyl-[2-(2-hydroxyethoxy)ethyl]amino} acetate (5.83 g, 16.5 mmol) as a colorless oily product with a yield of 63%.

$R_f$ 0.58 (ethyl acetate/methanol=20/1);
$^1$H NMR (500 MHz, ppm, $CDCl_3$) δ1.34 (d, 9H, J=54.5 Hz), 2.19 (brs, 1H), 3.38-3.45 (m, 4H), 3.50-3.60 (m, 4H), 3.99 (d, 2H, J=41.3 Hz), 5.09 (d, 2H, J=4.1 Hz), 7.25-7.30 (m, 5H); $^{13}$CNMR (125 MHz, ppm, $CDCl_3$) δ27.82, 28.05, 47.90, 48.20, 49.81, 50.39, 61.23, 66.42, 69.92, 72.12, 80.08, 127.93, 128.14, 135.25, 154.99, 155.19, 169.94, 170.07;
IR (neat, $cm^{-1}$) 3449, 2934, 2872, 1751, 1701, 1458, 1400, 1367, 1252, 1143;
Anal. Calcd for $C_{18}H_{27}NO_6$: C, 61.17; H, 7.70; N, 3.96. Found: C, 60.01; H, 7.75; N, 4.13.

[Second Step]:

Under an argon gas atmosphere, a tetrahydrofuran (20 mL) solution of benzyl{tert-butoxycarbonyl-[2-(2-hydroxyethoxy)ethyl]amino} acetate (5.83 g, 16.5 mmol) was added dropwise to a tetrahydrofuran (10 mL) solution of sodium hydride (1.2 g, 24.8 mmol, 50% in mineral oil) at 0° C. After stirring at the same temperature for 20 minutes, iodomethane (1.6 mL, 24.8 mmol) was added at 0° C. The reaction mixed liquid was stirred at room temperature for 20 hours and then water was added while cooling in an ice bath, thereby terminating the reaction. The reaction liquid was extracted three times with ether and the organic layer was dried, and then the residue was concentrated under reduced pressure and purified by silica gel flash column chromatography (eluent: hexane/ethyl acetate=5/1, 3/1) to obtain benzyl{tert-butoxycarbonyl-[2-(2-methoxyethoxy)ethyl]amino} acetate (3.02 g, 8.21 mmol) as a colorless oily product with a yield of 50%.

$R_f$ 0.54 (hexane/ethyl acetate=1/1);

$^1$H NMR (500 MHz, ppm, CDCl$_3$) δ1.34 (d, 9H, J=51.8 Hz), 3.28 (d, 3H, J=2.7 Hz), 3.37-3.46 (m, 6H), 3.52 (dt, 2H, J=5.4 Hz, 16.5 Hz), 4.02 (d, 2H, J=34.8 Hz), 5.09 (d, 2H, J=4.5 Hz), 7.24-7.30 (m, 5H); $^{13}$C NMR (125 MHz, ppm, CDCl$_3$) δ24.93, 25.16, 44.68, 45.00, 46.70, 47.40, 55.78, 63.30, 67.22, 68.60, 76.95, 124.98, 125.14, 125.36, 132.49, 151.99, 152.31, 166.84, 166.96;

IR (neat, cm$^{-1}$) 2880, 1751, 1701, 1560, 1458, 1400, 1366, 1117, 698, 617;

Anal. Calcd for C$_{19}$H$_{29}$NO$_6$: C, 62.11; H, 7.96; N, 3.81. Found: C, 62.15; H, 8.16; N, 3.83.

[Third Step]:

Under an argon atmosphere, trifluoroacetic acid (9.0 mL) was added to a dichloromethane (17 mL) solution of benzyl{tert-butoxycarbonyl-[2-(2-methoxyethoxy)ethyl]amino} acetate (3.02 g, 8.21 mmol), followed by stirring at room temperature for 7 hours. After adjusting the pH to 10 by adding an aqueous 10% sodium carbonate solution, the reaction liquid was extracted with dichloromethane and the organic layer was dried over anhydrous magnesium sulfate, and then the residue was concentrated under reduced pressure to quantitatively obtain benzyl[2-(2-methoxyethoxy)ethylamino] acetate (2.18 g, 8.19 mmol) as a yellow oily product.

$R_f$ 0.32 (ethyl acetate/methanol=20/1);

$^1$H NMR (500 MHz, ppm, CDCl$_3$) δ1.99 (brs, 1H), 2.83 (t, 2H, J=5.3 Hz), 3.38 (s, 3H), 3.50 (s, 2H), 3.54 (t, 2H, J=4.6 Hz), 3.60-3.62 (m, 4H), 5.17 (s, 2H), 7.32-7.38 (m, 5H); $^{13}$C NMR (125 MHz, ppm, CDCl$_3$) δ48.46, 50.66, 58.76, 66.20, 70.00, 70.44, 71.64, 128.09, 128.33, 135.44, 171.84;

IR (neat, cm$^{-1}$) 3350, 2876, 1736, 1560, 1458, 1117, 1030, 698, 619;

Anal. Calcd for C$_{14}$H$_{21}$NO$_4$: C, 62.90; H, 7.92; N, 5.24. Found: C, 62.28; H, 8.20; N, 5.05.

[Fourth Step]:

Activated carbon (219 mg) with palladium (10% by weight) supported thereon was added to a methanol (27 mL) solution of benzyl[2-(2-methoxyethoxy)ethylamino] acetate (2.19 g, 8.19 mmol) at room temperature, followed by purging with a hydrogen gas and further stirring under a hydrogen atmosphere at room temperature for 7 hours. Pd/C was removed through a glass filter over which a celite pad was spread, and the celite layer was washed with methanol and then the filtrate was concentrated under reduced pressure to obtain [2-(2-methoxyethoxy)ethylamino]acetic acid 1 (1.38 g, 7.78 mmol) as a yellow oily product with a yield of 95%.

$^1$H NMR (500 MHz, ppm, MeOD) δ3.21 (t, 2H, J=5.1 Hz), 3.38 (s, 3H), 3.51 (s, 2H), 3.57 (t, 2H, J=4.4 Hz), 3.65 (t, 2H, J=4.6 Hz), 3.73 (t, 2H, J=5.1 Hz); $^{13}$C NMR (125 MHz, ppm, MeOD) δ 48.13, 50.49, 59.16, 67.08, 71.05, 72.85, 171.10;

IR (neat, cm$^{-1}$) 3414, 2827, 1751, 1630, 1369, 1111, 1028, 851, 799;

Anal. Calcd for C$_7$H$_{15}$NO$_4$: C, 47.45; H, 8.53; N, 7.90. Found: C, 46.20; H, 8.49; N, 7.43.

Synthesis of Aldehyde 4

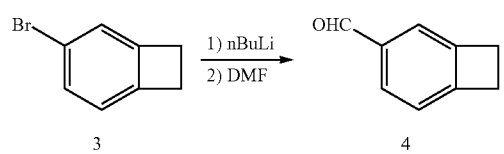

Under a nitrogen atmosphere, bromide 3 (3.0 g, 16.3 mmol) and 50 ml of anhydrous tetrahydrofuran were charged in a 50 ml recovery flask. After cooling to −78° C. under a nitrogen gas flow, 11.3 ml (18.0 mmol) of an n-butyl lithium hexane solution (1.59 M) was added dropwise, followed by stirring at the same temperature for 30 minutes. Then, 2.40 g of anhydrous dimethylformamide was added dropwise in the recovery flask, followed by stirring at the same temperature for 30 minutes, heating to room temperature and further stirring for 1 hour. The reaction liquid was poured into 100 ml of water and the oil phase was extracted twice with 50 ml of ethyl acetate, and then the oil phase was dried over anhydrous magnesium sulfate. After isolating the magnesium compound by filtration, the oil phase was concentrated under reduced pressure using an evaporator and the obtained residue was purified by silica gel chromatography (Wakosil C-300, eluent: hexane/ethyl acetate=3:1 (volume ratio)) to obtain 1.54 a (yield: 71.1%) of aldehyde 4 as the objective product.

$^1$H-NMR (270 MHz/CDCl$_3$):

δ3.24 (s, 4H), 7.21 (d, 1H), 7.57 (s, 1H), 7.72 (d, 1H), 9.93 (s, 1H)

Example 1

Synthesis of Fullerene Derivative A and Fullerene Derivative B

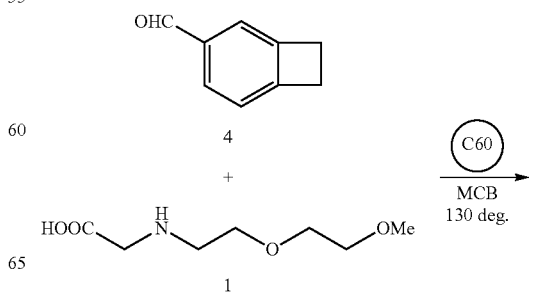

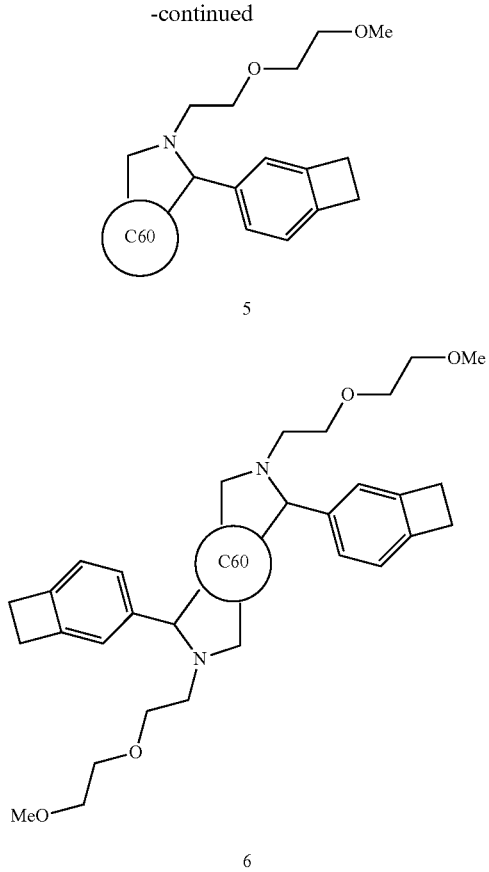

Under a nitrogen atmosphere, aldehyde 4 (0.19 g, 1.40 mmol), [2-(2-methoxyethoxy)ethylamino]acetic acid 1 (0.19 g, 1.04 mmol), C60 (0.50 g, 0.69 mmol) and chlorobenzene (30 ml) were charged in a 50 ml recovery flask, followed by stirring with heating under a nitrogen gas flow at 130° C. for 6 hours. After cooling the reaction liquid to room temperature, the reaction liquid was concentrated under reduced pressure using an evaporator. Then, a fullerene derivative was separated from the obtained residue using silica gel chromatography (Wakosil C-300). In the separation of the fullerene derivative, the unreacted C60 was separated and recovered using carbon disulfide ($CS_2$) as an eluent of silica gel chromatography. Then, the eluent was replaced by a mixed solvent of toluene and ethyl acetate and the ratio of the mixed solvent was changed from 100:0 (the volume ratio of toluene to ethyl acetate) to 90:10 (the volume ratio of toluene to ethyl acetate), and crystals containing the fullerene derivative were separated. The crystals were washed with 10 ml of methanol and dried under reduced pressure to obtain 80 mg (yield: 11.9%) of 5 (fullerene derivative A) as the objective product.

Then, the ratio of the mixed solvent of the eluent (toluene/ethyl acetate) was adjusted to 1:1 (volume ratio) and fractionation was carried out. The thus fractionated solution was concentrated, and the residue was washed with 10 ml of methanol and then dried under reduced pressure to obtain 116 mg in total of a fullerene derivative having two or more structures represented by formula (12). Examples of the fullerene derivative having two or more structures represented by formula (12) include 6 (fullerene derivative B).

The NMR analysis results of the fullerene derivative A are shown below.

$^1$H-NMR (270 MHz/CDCl$_3$):

δ2.82 (m, 1H), 3.16 (brs, 4H), 3.30-3.50 (m, 1H), 3.45 (s, 3H) 3.65 (m, 2H), 3.72-3.80 (m, 2H), 3.90-4.10 (m, 2H), 4.28 (d, 1H), 5.10 (s, 1H), 5.20 (d, 1H), 7.06 (d, 1H), 7.40-7.70 (brd, 1H).

Example 2

Production and Evaluation of Organic Thin-Film Solar Cell

As an electron donor, regioregular poly(3-hexylthiophene) (Lot No.: 09007 KH, manufactured by Aldrich Corp.) was dissolved in chlorobenzene in the concentration of 1% (% by weight). Then, the fullerene derivative A, which is an electron acceptor, was added to the solution so that the amount (by weight) thereof becomes equivalent to that of the electron donor. Then, the obtained mixture was filtered through a Teflon (registered trademark) filter having a pore diameter of 1.0 μm to prepare a coating solution.

A glass substrate provided with an ITO film having a thickness of 150 nm by a sputtering method was subjected to an ozone-UV treatment to perform a surface treatment. Then, the coating solution was spin-coated on the obtained glass substrate to obtain an active layer (film thickness of about 100 nm) of an organic thin-film solar cell. Then, the coated substrate was baked under a nitrogen atmosphere at 130° C. for 10 minutes. Lithium fluoride was vapor-deposited in a thickness of 4 nm thereon by a vacuum deposition apparatus, and then Al was vapor-deposited in a thickness of 100 nm. The degree of vacuum in vacuum deposition was 1 to $9 \times 10^{-3}$ Pa in both cases. The obtained organic thin-film solar cell had a shape of 2 mm×2 mm square. The open-circuit voltage and photoelectric conversion efficiency of the obtained organic thin-film solar cell were determined by measuring the current and voltage generated when the solar cell is irradiated with a predetermined dose of light using a solar simulator (manufactured by Bunkoukeiki Co., Ltd. under the trade name of "OTENTO-SUN II", AM 1.5G filter, irradiance: 100 mW/cm$^2$). The results of the open-circuit voltage are shown in Table 1. The photoelectric conversion efficiency was 3.0%.

Example 3

Production and Evaluation of Organic Thin-Film Solar Cell

In the same operation as in Example 2, except that the fullerene derivative A in Example 2 was changed to the fullerene derivative having two or more structures represented by the formula (12) produced in Example 1, the open-circuit voltage was measured. The results are shown in Table 1.

Comparative Example 1

Production and Evaluation of Organic Thin-Film Solar Cell

In the same operation as in Example 2, except that the fullerene derivative A in Example 2 was changed to a [60]-PCBM (phenyl C61-butyric acid methyl ester, manufactured by Frontier Carbon Corporation under the trade name of E100, Lot number: 9A0104A), the open-circuit voltage was measured. The results of the open-circuit voltage are shown in Table 1. The photoelectric conversion efficiency was 2.6%.

TABLE 1

|  | Fullerene derivative | Open-circuit voltage (Voc) |
| --- | --- | --- |
| Example 2 | Fullerene derivative A | 0.65 |
| Example 3 | Fullerene derivative having two or more structures represented by the formula (12) | 0.72 |
| Comparative Example 1 | [60]-PCBM | 0.59 |

INDUSTRIAL APPLICABILITY

The fullerene derivative of the present invention can be applied to an organic photoelectric conversion element having a high open-circuit voltage and is therefore suitable for an organic thin-film solar cell or an organic photosensor, and thus it is extremely useful.

The invention claimed is:

1. A fullerene derivative having a partial structure represented by formula (2a) or (2b):

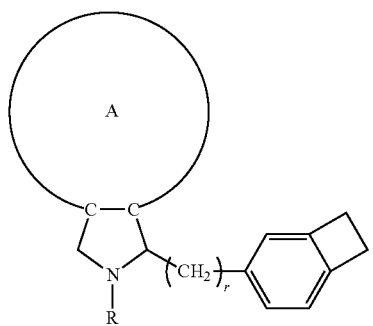
(2a)

wherein ring A represents a fullerene skeleton having 60 or more carbon atoms, and R is an alkyl group having 1 to 20 carbon atoms; an alkoxy group having 1 to 20 carbon atoms; an aryl group having 6 to 60 carbon atoms; a halogen atom; a heterocyclic group selected from the group consisting of a thienyl group, a pyridyl group, a furyl group, a piperidyl group, a quinolyl group, an isoquinolyl group and a pyrrolyl group; a group represented by formula (3):

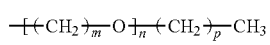
(3)

wherein m represents an integer of 1 to 6, n represents an integer of 1 to 4, p represents an integer of 0 to 5 and, when a plurality of structures represented by —(CH$_2$—)$_m$—O— are present, m in the structures may be the same numerical value, or mutually different numerical values; or a group having an ester structure represented by formula (4):

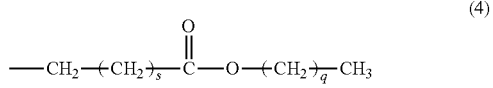
(4)

wherein s represents an integer of 0 to 10, and q represents an integer of 0 to 10 and r represents an integer of 0 to 4, and

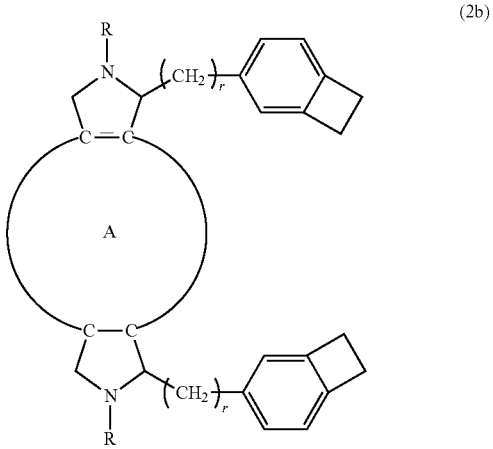
(2b)

wherein ring A represents a fullerene skeleton having 60 or more carbon atoms, R and r have the same meanings as defined above, a plurality of R's may be the same or different, and a plurality of r's may be the same or different.

2. The fullerene derivative according to claim 1, wherein R is a group represented by formula (3):

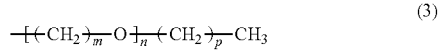
(3)

wherein m represents an integer of 1 to 6, n represents an integer of 1 to 4, p represents an integer of 0 to 5 and, when a plurality of structures represented by —(CH$_2$—)$_m$—O— are present, m in the structures may be the same numerical value, or mutually different numerical values.

3. A composition comprising the fullerene derivative according to claim 1 and a polymer compound.

4. The composition according to claim 3, wherein the polymer compound is a polymer compound having a repeating unit selected from the group consisting of repeating units represented by formulas (10) and (11):

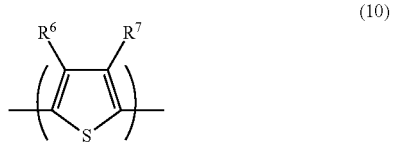
(10)

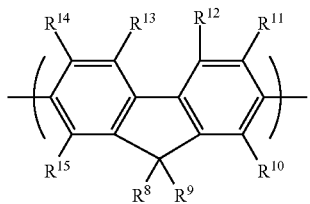

(11)

wherein $R^6$, $R^7$, $R^8$, $R^9$, $R^{10}$, $R^{11}$, $R^{12}$ $R^{13}$, $R^{14}$ and $R^{15}$ are the same or different and represent a hydrogen atom, an alkyl group, an alkoxy group or an aryl group.

5. An organic photoelectric conversion element comprising an anode, a cathode, and a layer containing the fullerene derivative according to claim 1 formed between the anode and the cathode.

6. An organic photoelectric conversion element comprising an anode, a cathode, and a layer containing the fullerene derivative according to claim 3 formed between the anode and the cathode.

7. A method for producing an organic photoelectric conversion element comprising an anode, a cathode, and an active layer formed between the anode and the cathode, the method comprising applying a solution containing the fullerene derivative according to claim 1 and a solvent on the anode or the cathode to form an organic layer, and then heating the organic layer to form the active layer.

8. A method for producing an organic photoelectric conversion element comprising an anode, a cathode, and an active layer formed between the anode and the cathode, the method comprising applying a solution containing the composition according to claim 3 and a solvent on the anode or the cathode to form an organic layer, and then heating the organic layer to form the active layer.

9. The fullerene derivative according to claim 1 which has one to four structures represented by formula 2(a) or 2(b).

* * * * *